United States Patent

Noguchi et al.

[11] Patent Number: 5,546,493
[45] Date of Patent: Aug. 13, 1996

[54] OPTICAL WAVEGUIDE

[75] Inventors: Tomoko Noguchi, Kodaira; Kazuo Naito, Kawasaki; Tasuku Saito, Tokorozawa; Ryo Sakurai; Minoru Ishiharada, both of Kodaira, all of Japan

[73] Assignee: Bridgestone Corporation, Tokyo, Japan

[21] Appl. No.: 364,495

[22] Filed: Dec. 27, 1994

[30] Foreign Application Priority Data

Dec. 27, 1993 [JP] Japan .................. 5-348623

[51] Int. Cl.⁶ .................................. G02B 6/20
[52] U.S. Cl. .......................... 385/125; 385/143
[58] Field of Search .............. 428/321.1, 321.5; 385/141–145, 125

[56] References Cited

U.S. PATENT DOCUMENTS 5,412,750  5/1995  Nath .................. 385/125

FOREIGN PATENT DOCUMENTS 62-231904  10/1987  Japan .

OTHER PUBLICATIONS

Marder et al; ACS symposium Series 455; 1991; pp. 113–127 and 258–266.

Primary Examiner—John Ngo
Attorney, Agent, or Firm—Sughrue, Mion, Zinn, Macpeak & Seas

[57] ABSTRACT

In an optical waveguide comprising a transparent cladding (1) filled with a transparent liquid core (2) having a higher refractive index than the cladding, a liquid consisting of an oligomer having a phosphazene skeleton, typically phosphazene oil is used as the core (2). The waveguide is well resistant to heat and weathering, ensures stable performance in a wide temperature range over a long period of time, and provides good light transmission in a wide wavelength range covering the UV, visible and IR spectra.

1 Claim, 3 Drawing Sheets

PHOSPHAZENE OIL HI-14

PHOSPHAZENE OIL HI-21

OPTICAL WAVEGUIDE

BACKGROUND OF THE INVENTION

1. Field of the Invention

This invention relates to an optical waveguide including a transparent cladding filled with a transparent liquid core having a higher refractive index than the cladding,

2. Prior Art

Solution type optical waveguide tubes comprising a flexible transparent hollow member internally filled with a liquid core are well known in the art. A typical basic structure is shown in FIG. 1 wherein a cylindrical flexible tubing or cladding 1 is internally filled with a liquid core 2 having a higher refractive index than the cladding. The cladding 1 has opposite open ends (only one end shown) in which a window member 3 is fitted for closing the end for containing the liquid core 2 in the cladding 1 in a sealed manner. The window member 3 is a cylindrical transparent solid plug which serves for suitable optical functions of guiding incident or emergent light. The cladding 1 is fastened to the window member 3 by a terminal clamp 4.

One exemplary solution type optical waveguide tube is disclosed in Japanese Patent Publication No. 231904/1987 as a high efficiency optical waveguide comprising a liquid core and a cladding of a polymer having a lower index of refraction than the core liquid. In such high efficiency optical waveguides, fluorinated rubber, fluorocarbon resins, silicone rubber, and butyl rubber are conventionally used as the cladding material, and phosphate oils, fluorinated oils and silicone oils are used as the core material. The material of which the core of optical waveguides is formed should desirably have minimized light absorption in the wavelength spectrum of light to be transmitted, improved light transmittance, and a wide service temperature range, and undergo little interaction with the cladding material (swelling, dissolution, reaction, etc.). However, the phosphate oils conventionally used as the core material, for example, trioctyl phosphate (TOP) have the disadvantages of degradation and yellowing at temperatures above 80° C. interaction with silicone materials used as the cladding even at room temperature, remarkable absorption in the near-infrared region, and poor light transmittance. As compared with the phosphate oils, the fluorinated oligomers are optically superior and heat resistant. The fluorinated oligomers, however, have the risk of interaction with cladding materials, especially fluorinated materials at elevated temperatures. The silicone oils also suffers from the risk of interaction with cladding materials at elevated temperatures.

Therefore it is desired to overcome the above-mentioned problems associated with the core material of optical waveguides.

SUMMARY OF THE INVENTION

Searching for a liquid suitable as the core of an optical waveguide, we have found that an oligomer having a phosphazene skeleton is an optimum material. In connection with an optical waveguide wherein a transparent cladding is internally filled with a transparent liquid core having a higher refractive index than the cladding, we have found that when a liquid consisting of an oligomer having a phosphazene skeleton is used as the core, there is obtained an improved optical waveguide having improved heat resistance and weather resistance, maintaining stable performance in a wide temperature range over a long period of time, and having good light transmittance over a wide wavelength range.

More particularly, the oligomer having a phosphazene skeleton is well heat resistant, flame retardant, inflammable, lubricating, free of the risks of degradation, contamination and corrosion, chemically inert, non-deleterious to various thermoplastic resins, low in vapor pressure, compatible with various solvents, and resistant to chemicals. Additionally the oligomer which undergoes little interaction with various rubbers and fluorocarbon resins is free of or minimal in harmonics of C—H stretching vibration, and has a refractive index which largely varies with a functional group in the oligomer molecule. Therefore, when a liquid comprising the phosphazene skeleton oligomer having these advantages is used as the core of the optical waveguide, the core is not degraded or yellowed at elevated temperatures, undergoes no interaction (such as swelling, dissolution and reaction) with the cladding material, maintains its performance stably over a long term, exhibits high light transmittance in a wide wavelength range covering the ultraviolet, visible and infrared spectra, and has a wide range of refractive index so that any desired angular aperture may be selected for a particular purpose. The resulting optical waveguide can be used in a variety of applications as a light transmitting tube.

DETAILED DESCRIPTION OF THE INVENTION

Figure 1:
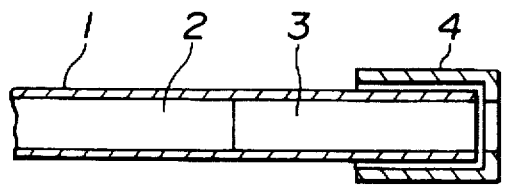
FIG. 1 is an axial cross-sectional view of an end portion of an optical waveguide according to one embodiment of the invention.
Figure 2:
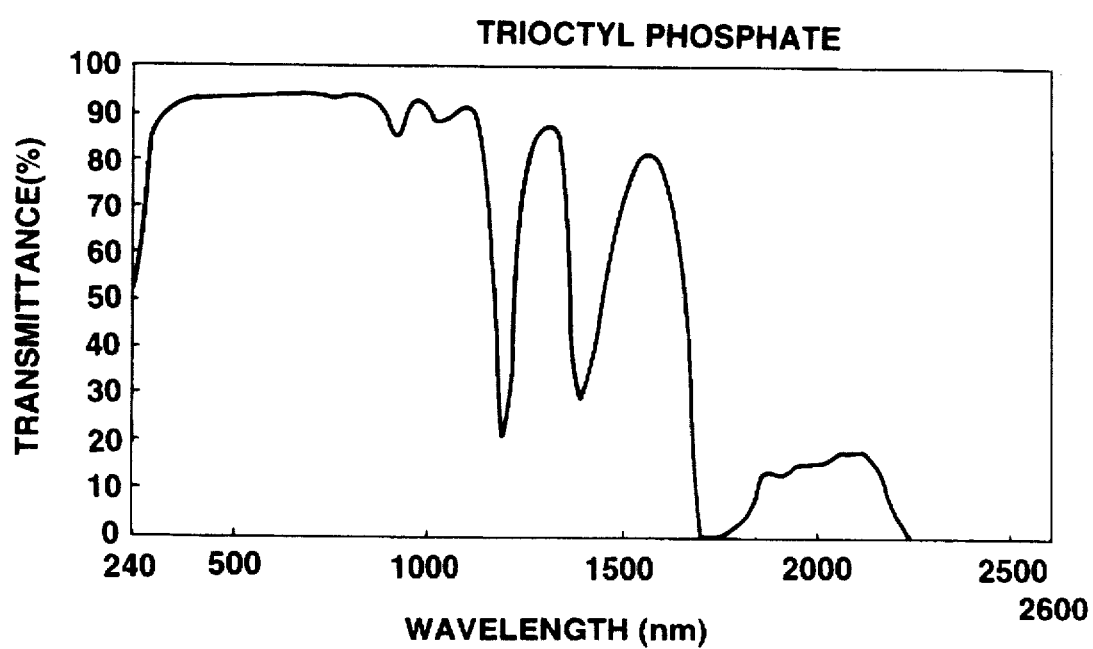
FIG. 2 is a graph showing the light transmission spectrum of a phosphate oil (TOP).
Figure 3:
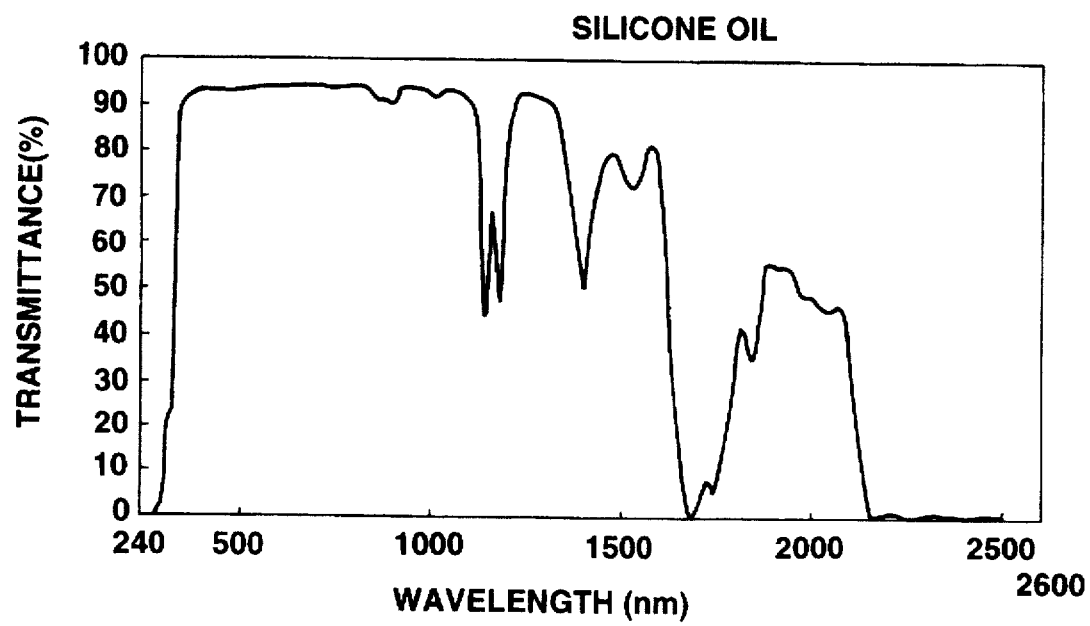
FIG. 3 is a graph showing the light transmission spectrum of a silicone oil with n=1.50.
Figure 4:
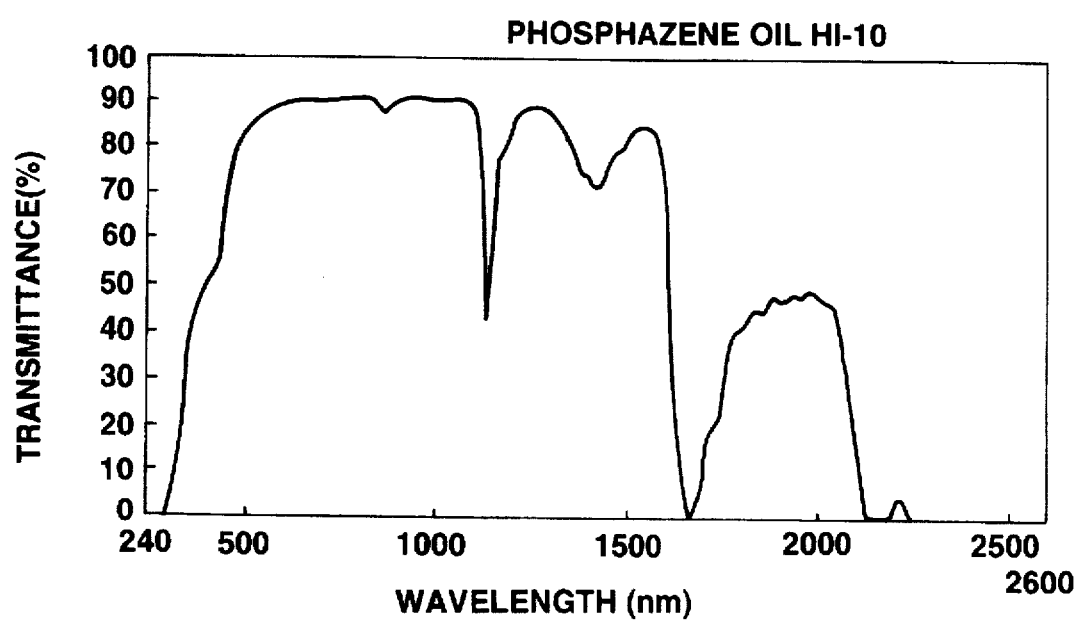
FIG. 4 is a graph showing the light transmission spectrum of phosphazene oil HI-10 with n=1.526.
Figure 5:
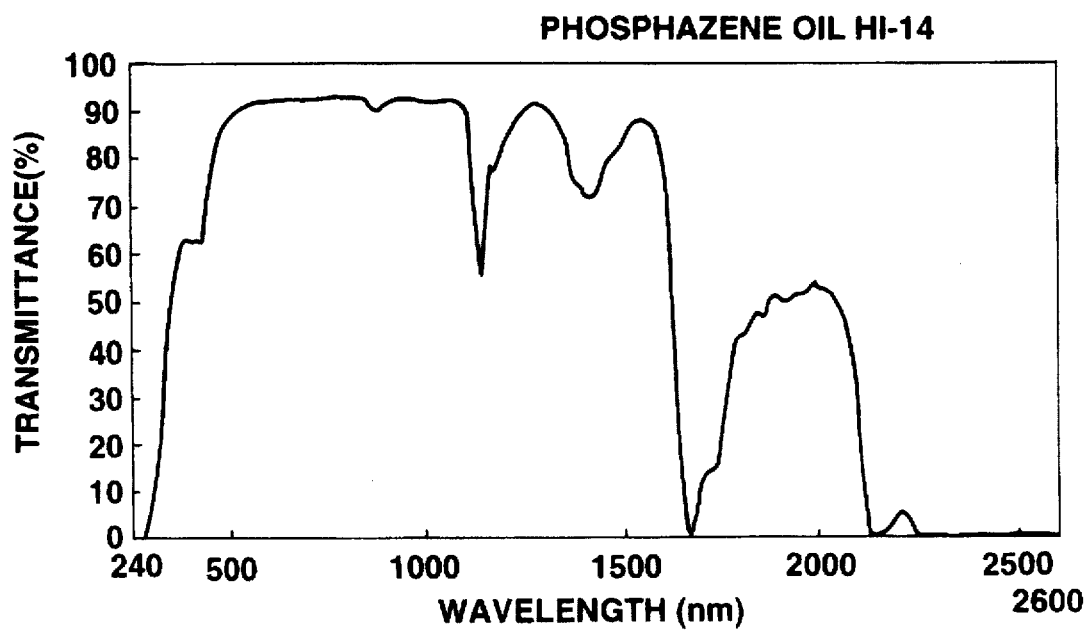
FIG. 5 is a graph showing the light transmission spectrum of phosphazene oil HI-14 with n=1.468.
Figure 6:
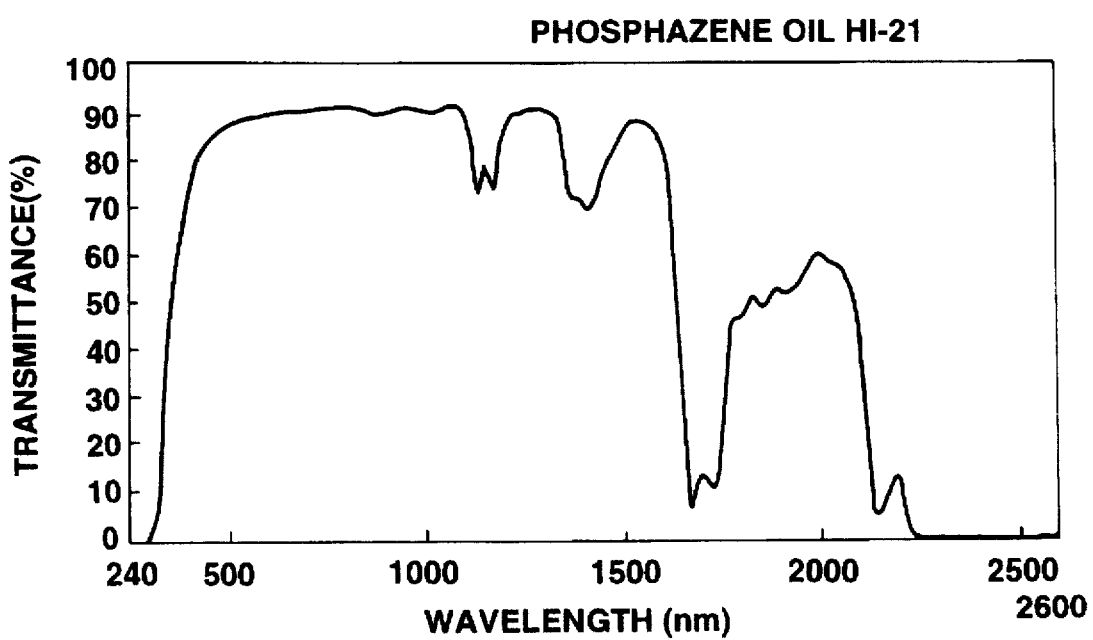
FIG. 6 is a graph showing the light transmission spectrum of phosphazene oil HI-21 with n=1.398.

The present invention pertains to an optical waveguide comprising a transparent cladding internally filled with a transparent liquid core having a higher refractive index than the cladding. This optical waveguide may be of the same basic structure as the prior art solution type light transmitting tube shown in FIG. 1. A length of cylindrical cladding 1 is internally filled with a liquid core 2 having a higher refractive index than the cladding. Each open end of the cladding is closed with a window plug 3 fitted therein and fastened thereto by a terminal clamp 4.

The cladding 1 may be made of a transparent material which is flexible, formable into a tubular form, and has a low refractive index, for example, such as plastics and elastomers. Illustrative examples of the cladding material include polyethylene, polypropylene, polyamide, polystyrene, ABS resins, polymethyl methacrylate, polycarbonate, polyvinyl chloride, polyvinylidene chloride, polyvinyl acetate, polyethylene-vinyl acetate copolymers, polyvinyl alcohol, polyethylene-polyvinyl alcohol copolymers, fluorocarbon resins, silicone resins, natural rubber, polyisoprene rubber, polybutadiene rubber, styrene-butadiene copolymers, butyl rubber, halogenated butyl rubber, chloroprene rubber, acrylic rubber, EPDM, acrylonitrilebutadiene copolymers, fluorinated rubber, silicone rubber, and polyurethane.

Preferred among these are silicone polymers and fluorinated polymers having a lower refractive index. Exemplary preferred silicone copolymers are dimethylsiloxane polymers, methylphenylsiloxane polymers, and fluoro-silicone polymers. Exemplary preferred fluorinated polymers are polytetrafluoroethylene (PTFE), tetrafluoroethylene-hexafluoropropylene copolymers (FEP), tetrafluoroethyleneperfluoro-alkoxyethylene copolymers (PFE), polychloro-trifluoroethylene (PCTFE), tetrafluoroethylene-ethylene copolymer (ETFE), polyvinylidene fluoride, polyvinyl fluoride, vinylidene fluoride-trifluoroethylene chloride copolymers, vinylidene fluoride-hexafluoropropylene copolymers, vinylidene fluoride-hexafluoro-propylene-tetrafluoroethylene terpolymers, tetrafluoroethylenepropylene rubber, and fluorinated thermoplastic elastomers.

These materials may be used alone or in admixture of two or more. Either a single tube or a double-wall tube may be used. Only the inner surface of the tube which is to contact the core may be smoothed by a suitable technique such as coating and double extrusion.

For the purpose of light shielding, the outer surface of the cladding may be covered with a sheath of an opaque material.

The core 2 is formed of a transparent liquid comprising an oligomer having a phosphazene skeleton. The oligomer preferably has the following structure.

$$+P=N)_n- \quad\quad (1)$$
with $X^1$ above P and $X^2$ below P.

In formula (1), $X^1$ and $X^2$ are independently selected from the group consisting of an alkoxy group having 1 to 6 carbon atoms, an aryloxy group having 6 to 10 carbon atoms (e.g., phenoxy), $-NH_2$, $-NHR$, $-NR_2$, $-O-C_mF_{2m+1}$, and $-Cl$ wherein R is an alkyl group having 1 to 6 carbon atoms, letter m is a number of 1 to 6, and letter n is the polymerization number.

In the practice of the invention, it is preferred that a cyclic oligomer of formula (1) wherein n=3 is present as a main component among the oligomers. Illustrative are the following phosphazene oils of formula (1) wherein n=3. Ph is a phenyl group.

Phosphazene oil: HI-10

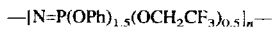

Phosphazene oil: HI-14

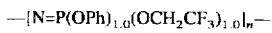

Phosphazene oil: HI-21

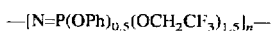

It is noted that the oligomer having a phosphazene skeleton as the core material should have a higher refractive index than the cladding material used. The refractive index largely varies with a functional group. Those oligomers having $-O-C_6H_5$ and $-OCH_2CF_3$ in side chains change their refractive index with the ratio of these groups as shown below. Therefore, where the oligomer is used as the core material, the refractive index can be changed by properly selecting its side chains insofar as its refractive index is larger than that of the cladding material. It is then possible to select the angular aperture of the optical waveguide depending on a particular purpose.

| a:b | 1.5:0.5 | 1.0:1.0 | 0.5:1.5 |
|---|---|---|---|
| refractive index | 1.526 | 1.468 | 1.398 |

The window plug 3 is formed of a material which has minimum light absorption in a desired wavelength range, especially that transmits ultraviolet radiation, visible radiation and infrared radiation. The window plug materials are typically transparent materials including crown glass, silica glass, flint glass, chalcogenide glass, sapphire, quartz, polycarbonate, methacrylic resin, silicone resin, fluorocarbon resin, and polystyrene resin. In an embodiment wherein light is radiated from the outer periphery of the tube, the plug may be made of an opaque material such as ceramics.

There has been described an optical waveguide which is well resistant to heat and weathering, ensures stable performance in a wide temperature range over a long period of time, and provides good light transmittance in a wide wavelength range covering the ultraviolet, visible and infrared spectra. It is suitable as high energy radiation transmitting tubes, for example, image guides for optical communication and endoscopes, light guides for light of various wavelengths including ultraviolet, visible and infrared radiation, and light transmission tubes in sunlight utilizing systems such as marine farms, vegetable plants and urban apartments. It will find particular use in infrared radiation transmitting systems and near-ultraviolet light utilizing equipment.

EXAMPLE

Examples of the present invention are given below by way of illustration and not by way of limitation.

EXAMPLE 1—3 & COMPARATIVE EXAMPLES 1—3

Optical waveguide tubes of the structure shown in FIG. 1 were prepared using fluorinated rubber, silicone rubber or butyl rubber as the cladding and quartz glass as the window plugs. The materials used as the core are shown below.
Core
Phosphate oil: TOP(trioctyl phosphate)
Fluorinated oil: $-[CF_2C(Cl)F]_n-$ (n=500)
Silicone oil:

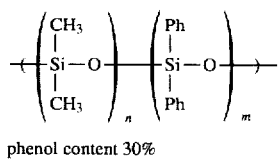

phenol content 30%

Phosphazene:
Phosphazene oil HI-10

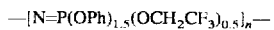

Phosphazene oil HI-14

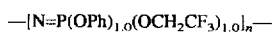

Phosphazene oil HI-21

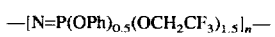

n=3

A first set of the optical waveguide tubes were allowed to stand at room temperature for 80 hours. A second set of the optical waveguide tubes were heated at 80° C. for 5 hours. The optical waveguide tubes of the first and second sets were measured for volume swell and examined for interaction between the cladding and the core. The results are shown in Tables 1 and 2.

TABLE 1

| room temperature/ 80 hr. Core material | Cladding material | | | |
|---|---|---|---|---|
| | Fluorinated rubber | Silicone rubber | Butyl rubber | |
| Phosphate oil | 1.09 | 2.4 | 1.12 | CE1 |
| Fluorinated oil | 1.00 | 1.64 | 1.00 | CE2 |
| Silicone oil | 1.00 | 1.40 | 1.26 | CE3 |
| Phosphazene oil HI - 10 | 1.00 | 1.00 | 1.00 | E1 |
| Phosphazene oil HI - 14 | 1.00 | 1.03 | 1.03 | E2 |
| Phosphazene oil HI - 21 | 1.00 | 1.00 | 1.03 | E3 |

TABLE 2

| heated 80° C./5 hr. Core material | Cladding material | | | |
|---|---|---|---|---|
| | Fluorinated rubber | Silicone rubber | Butyl rubber | |
| Phosphate oil | 1.09 | 1.82 | 1.16 | CE1 |
| Fluorinated oil | 1.16 | 1.82 | 1.12 | CE2 |
| Silicone oil | 1.12 | 1.60 | 1.12 | CE3 |
| Phosphazene oil HI - 10 | 1.03 | 1.00 | 1.00 | E1 |
| Phosphazene oil HI - 14 | 1.03 | 1.06 | 1.03 | E2 |
| Phosphazene oil HI - 21 | 1.00 | 1.06 | 0.97 | E3 |

It is evident from Tables 1 and 2 that the tubes using phosphate oil, fluorinated oil and silicone oil as the core (Comparative Examples 1, 2 and 3) are easily swelled even at room temperature whereas the tubes using phosphazene oil as the core (Examples 1 to 3) undergo little or no swelling even when heated at an elevated temperature.

The phosphate oil (TOP), silicone oil (n=1.50), phosphazene oils HI-10 (n=1.526), HI-14 (n=1.468), and HI-21 (n=1.398) used as the core were measured for light transmission spectrum using a quartz cell of 10 mm wide. The results are shown in FIGS. 2 to 6.

It is seen that as compared with the spectra of phosphate oil and silicone oil (FIGS. 2 and 3), the spectra of phosphazene oils (FIGS. 4 to 6) have less absorption in the near-infrared region. It is thus evident that the phosphazene oils have minimal absorption at about 800 to 1100 cm$^{-1}$ and good light transmittance and are thus optimum core materials.

Japanese Patent Application No. 5-348623 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. An optical waveguide comprising a transparent liquid core having a higher refractive index than said cladding, wherein said core is a liquid selected from the group consisting of phosphazene oil HI-10, phosphazene oil HI-14, and phosphazene oil HI-21.

* * * * *